(12) United States Patent
DeAngelis (10) Patent No.: US 6,497,233 B1
(45) Date of Patent: Dec. 24, 2002

(54) ONE-PIECE STERILE DRAPE FOR USE ON SURGICAL INSTRUMENT CARTS

(76) Inventor: Luciano S. DeAngelis, PMB No. 258, 7101 N. Mesa Dr., El Paso, TX (US) 79912

( * ) Notice: Subject to any disclaimer, the term of this patent is extended or adjusted under 35 U.S.C. 154(b) by 0 days.

(21) Appl. No.: 09/805,716

(22) Filed: Mar. 13, 2001

(51) Int. Cl.[7] .............................................. A61B 19/00
(52) U.S. Cl. ...................................... 128/849; 128/855
(58) Field of Search ................................. 128/849–856

(56) References Cited

U.S. PATENT DOCUMENTS

| | | | |
|---|---|---|---|
| 270,443 A | 1/1883 | Kraemer | |
| 3,561,439 A | * 2/1971 | Bayer | |
| 3,766,913 A | * 10/1973 | Balin | 128/853 |
| 3,889,667 A | * 6/1975 | Collins | 128/855 |
| 3,955,569 A | * 5/1976 | Krzewinski | 128/132 |
| 4,627,363 A | * 12/1986 | Jones | 108/90 |
| 4,948,154 A | 8/1990 | Guggenheim | |
| 5,379,703 A | 1/1995 | Marshall | |
| 5,436,053 A | 7/1995 | Herum | |
| 5,546,960 A | * 8/1996 | Ishikawa | 318/587 |
| 5,778,890 A | * 7/1998 | Lofgren et al. | 128/849 |
| 5,832,927 A | * 11/1998 | Wijesinghe et al. | 128/849 |
| 5,860,420 A | * 1/1999 | Wiedner et al. | 128/853 |
| 6,019,102 A | 2/2000 | Becker | |
| 6,189,459 B1 | 2/2001 | DeAngelis | |

* cited by examiner

*Primary Examiner*—Michael A. Brown
*Assistant Examiner*—Lalita M. Hamilton
(74) *Attorney, Agent, or Firm*—Rod D. Baker (57) ABSTRACT

A disposable drape for use in covering dual-tier surgical carts used in hospital operating rooms. The drape is adapted to be placed upon both shelves of a surgical or medical cart having two shelves—an auxiliary shelf situated above a larger main shelf or table. The drape is intended to be sterile, and is provided with absorbent surfaces at locations corresponding to the tup surfaces of the cart's shelves when the drape is properly installed upon the cart. The drape is seamless. Pull tabes are provided to aid in the installation of the drape upon a cart without compromising drape sterility.

20 Claims, 6 Drawing Sheets

ONE-PIECE STERILE DRAPE FOR USE ON SURGICAL INSTRUMENT CARTS

BACKGROUND OF THE INVENTION

1. Field of the Invention (Technical Field)

The present invention relates to a specialized drape for use on surgical instrument tables or carts in hospital operating rooms, particularly to a sterile drape for use on a two-tiered instrument cart.

2. Background Art

During most medical surgeries, the surgeon must have convenient access to numerous surgical instruments. Often, the instruments are disposed upon a sterilized wheeled cart (or sometimes a wheelless table) situated in the operating room, near the operating room table. The cart has one or more shelves upon which the surgical instruments are placed for ready access.

In complex surgeries, so many instruments may be required that more than one shelf are required to hold all the instruments for ready use. Accordingly, presently in the art, more than one cart may be used, which crowds the operating room and complicates efforts to maintain the sterility of the operating area. Alternatively, operating room personnel may place instruments upon more than one tray, and then stack the trays one upon another on a single cart, which unfortunately complicates access to the instruments. Un-stacking and re-stacking trays of instruments upon a single cart takes too much time and increases the possibility of mishaps. Still, there is a need for rapid and ready access to all the instruments, without needlessly cramping the work area in the operating room with multiple carts—especially in smaller operating rooms.

In order to promote the ready accessibility of surgical instruments and tools during an operation, multi-tier instrument carts are frequently used in operating rooms. Increasingly popular for their versatility, multi-tier instrument carts and tables typically feature a main table-top surface and a smaller auxiliary shelf disposed parallel to and above the main surface. The main and auxiliary surfaces are mounted upon a frame that typically is wheeled for convenient movement about the hospital. The wheels often are lockable against rotation to secure the cart when in use. The main table surface provides a generously sized surface area to hold instruments at a convenient hip or waist-high level. These two-tier carts, sometimes called "back instrument tables," feature one auxiliary shelf having a top surface area somewhat less in size than the top surface area of the main surface; conventionally, the auxiliary shelf has the same length (right-to-left) as the main surface, but is considerably narrower in front-to-back dimension. The shelf is spaced above the main surface, and is situated rearward on the cart in relation to the main surface, so that the auxiliary shelf overhangs the back approximately one-third to one-half of the main surface. A suitable multi-tier operating room cart is described in detail in U.S. Pat. No. 6,189,459 to DeAngelis, all the teachings of which are incorporated herein by reference.

Another challenge in surgical operating rooms is the preservation of the sterile field. It is important to provide a sterile field that includes all auxiliary tables and carts upon which surgical instruments are arrayed for access by operating room personnel. It is known, for example, to provide covers for hospital gurneys and tables, such as the cover shown in U.S. Pat. No. 5,436,053 to Herum, and to provide some means for securing a cover to a table, such as that disclosed in U.S. Pat. No. 4,627,363 to Jones.

The popularity of two-tier operating room carts, coupled with the demand that the instrument surfaces of such carts be sterile, has presented some challenges. Operating room personnel appreciate the order and convenience offered by dual-tier instrument carts, but assuring that the two instrument surfaces are sterile before the placement of tools thereon has proven problematic. Sterility of instrument cart surfaces sometimes is provided by placing a sterile drape upon each of the cart's instrument surfaces. Placement of sterile drapes on two-tier carts, however, is complicated by the duel-surface configuration. For example, it is extremely preferable to cover not only the horizontal surfaces upon which the instruments will be situated, but also to provide a sterile barrier in front of the frame members supporting the auxiliary shelf. Thus, in order to maintain the integrity of the overall sterile field, some sort of vertically situated panel preferably is provided to extend down from the upper auxiliary shelf to the main table surface, so that a sterile shield is disposed between the main table surface and the frame components that support the upper auxiliary shelf. One effort to meet the challenge is simply to provide two drapes; a bottom section to cover the main instrument surface, and a top section for covering the upper auxiliary shelf surface. The top section then may be provided with a middle or curtain portion that hangs down to come into contact with the bottom section. This type of two-section drape is suggested in U.S. Pat. No. 6,189,459 to DeAngelis, currently co-owned by the applicant. Another two-piece type of drape is described in U.S. Pat. No. 6,019,102 to Becker.

Two-section drapes suffer from a number of drawbacks, most of all their complexity and/or cost of manufacture. The '102 patent to Becker, for example, teaches a two-section drape characterized as having either a "two-piece" or a "one piece" embodiment. Both the "one-piece" and the two-piece embodiments, however, are fashioned from multiple sections of drape material; Becker's "one-piece" embodiment is substantially identical to his two-piece embodiment, except that a manufactured seam is provided along the line where the two pieces are permanently joined together. The seam is along an edge of a vertically hanging portion of the top section, where it is joined to the horizontal surface of the bottom section at the time of manufacture. (In the two-piece embodiment, the top section is allowed to hang down into abutting contact with the bottom section, without being affixed thereto.) Thus, the manufactured seam of the "one-piece" embodiment of the Becker device is a complicated, expensive juncture; an edge of the top section must be joined to a plain, broad surface of the bottom section, with the result that the seam joins mutually perpendicular sections when the drape is in use. Not only does such a seam significantly complicate the manufacturing method of the Becker device, but the seam is subjected to considerable stresses while the drape is being placed on the dual-tier cart and/or while the drape and cart are in use. If the seam fails, the edge of the top section may tear away from the working surface of the bottom section, which may compromise the sterile field.

Operating room personnel sometimes resort to merely arranging an array of sterilized towels upon cart shelves to provide a sterile, absorbent working surface. Towels suffer from the need to be laundered and sterilized for later re-use, and also have no impermeable layer to prevent fluids from undesirably soaking through to the metal surfaces of the shelves.

A significant need remains for a simple, inexpensive, easy-to-use sterile drape for covering dual-tier operating room carts. Against the foregoing background, the present invention was developed.

SUMMARY OF THE INVENTION
(DISCLOSURE OF THE INVENTION)

There is provided according to the invention a special custom drape for placement upon a two-tier cart to provide a sterile covering for working surfaces of the cart, and a method for manufacturing the drape. The drape includes several special features which permit it to be handled, placed upon the auxiliary shelf, and secured in place with minimal challenges to sterility and to maintain the sterile field in the operating room.

According to the apparatus of the invention a drape is provided for use in covering a two-tier medical cart, the cart having a main shelf, an auxiliary shelf, and vertical support members extending between the shelves, the drape comprising a seamless foundation substrate comprising a sheet of flexible, impermeable plastic having an upper absorbent portion, a medial portion, a lower absorbent portion, and a lower skirt portion; a first absorbent surface disposed upon the substrate to define the upper absorbent portion; and a second absorbent surface disposed upon the substrate separate from the first absorbent surface to define the lower absorbent portion, wherein the medial portion comprises a portion of the substrate uncovered by an absorbent surface, between the upper absorbent portion and the lower absorbent portion, and also wherein the lower skirt comprises a portion of the substrate uncovered by an absorbent surface, and the lower absorbent portion is between the skirt and the medial portion. The upper absorbent portion has side edges and is folded and adhered along the side edges to define an envelope for receiving the auxiliary shelf. The first absorbent surface and the second absorbent surface each comprises a permeable plastic matrix layer and an absorbent layer intermediate between the substrate and the matrix layer, the matrix and absorbent layers pressed parallel together and adhered to the substrate. The drape preferably also features flexible side flaps extending from the medial layer, the side flaps being wrappable around the cart's vertical support members. The preferred embodiment of the drape apparatus has at least two flexible pull tabs, extending from the upper absorbent portion, for allowing the drape to be manipulated without handling the upper absorbent portion, the medial portion, the lower absorbent portion, and the lower skirt portion. The pull tabs preferably are two pairs of pull tabs, a pair extending from opposite sides of the upper absorbing portion, and each tab ideally has a lateral perforation permitting each the tab to be torn along the perforation for detachment from the upper absorbent portion. The drape also has at least one adhesive fastener disposed upon the first absorbent surface on the upper absorbent portion, wherein when the drape is installed upon the cart, the medial portion may be drawn into adhesive contact with the at least one adhesive fastener to maintain the medial portion pulled away from the lower absorbent portion.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED
EMBODIMENTS (BEST MODES FOR
CARRYING OUT THE INVENTION)

The present invention is of a truly one-piece surgical drape apparatus for use on dual-tier carts in medical operating rooms. The present invention is manufactured by an innovative method which permits the drape to be of integral, seamless construction, and yet completely cover a dual-tier cart in a manner consistent with operating room sterility protocols.

Figure 1:
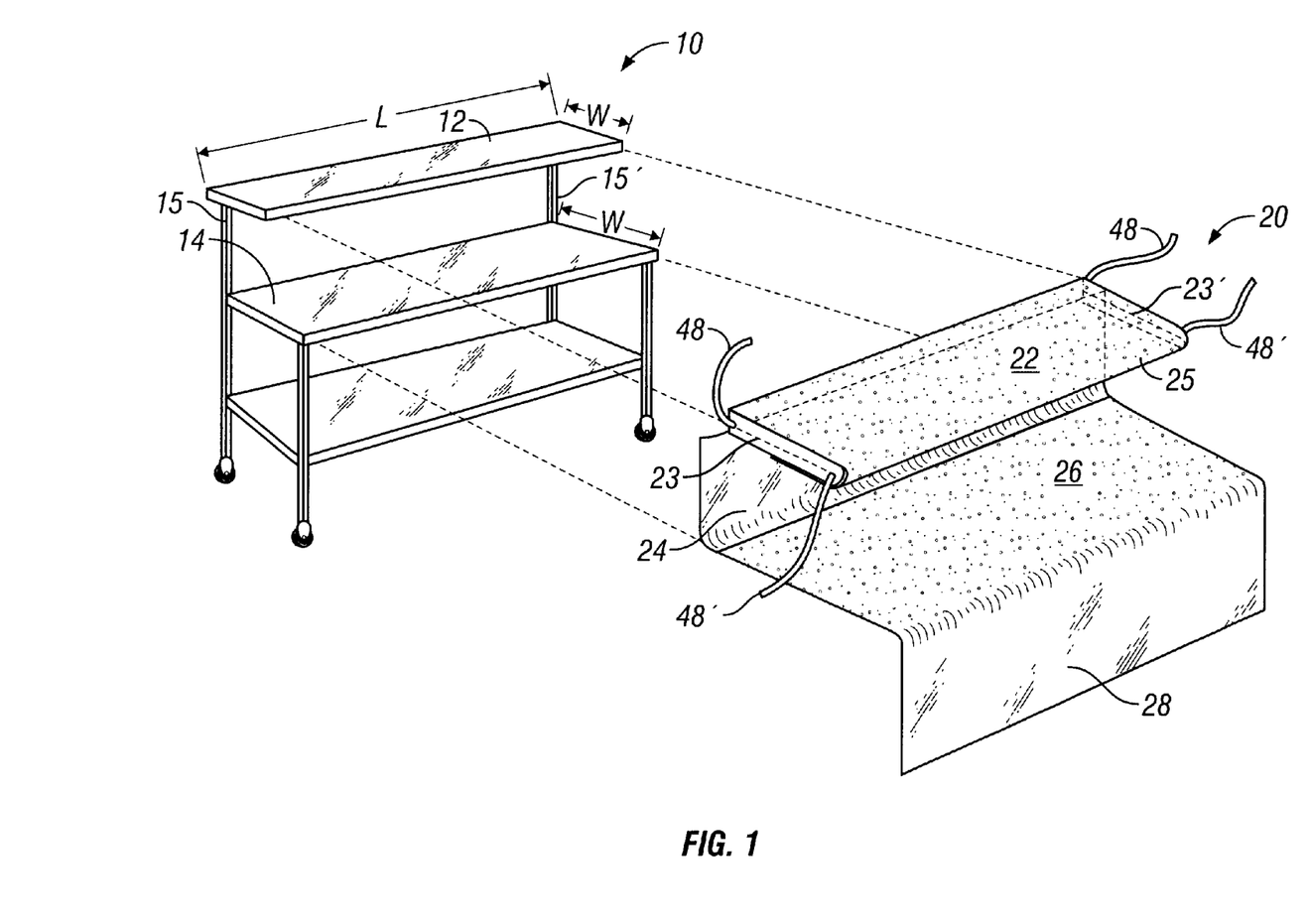
FIG. 1 is a perspective view of a preferred embodiment of the drape apparatus according to the invention, and illustrating how the inventive drape may be installed upon a two-tiered medical cart of conventional configuration.

FIG. 1 shows a two-tier instrument cart 10 commonly used in medical operating rooms to hold and display surgical instruments during surgery. The two-tier cart 10 features an auxiliary or upper shelf 12 disposed parallel above the main shelf 14. Ordinarily, the auxiliary shelf 12 is narrower, front-to-back, than the main shelf 14, but the shelves commonly are equal in side-to-side length. Operating room personnel place instruments on both shelves 12, 14 so to be present and available in an orderly and convenient manner for access and use during the medical procedure. The frame of the cart 10 includes vertical back support members 15, 15' that provide structural stability to the cart and serve to support the auxiliary shelf 12 in a cantilevered manner, as indicated in FIG. 1. The auxiliary shelf 12 thus overhangs the main shelf 14 so that objects placed on the upper shelf 12 are readily visible and accessible, yet without compromising the visibility and accessibility of objects upon the main shelf 14. It is essential that the upwardly facing working surfaces of both shelves 12, 14 be sterile before receiving thereon the sterilized surgical tools. While in theory the actual surfaces of the shelves 12, 14 could be sterilized for use, this is impractical, disfavored, and rarely if ever practiced. Moreover, it is desirable that the working surfaces of the shelves 12, 14 offer a measure of absorbency whereby fluids on the instruments and tools are absorbed, which bare stainless steel shelves 12, 14 cannot offer.

Perhaps of paramount advantage is that the drape 20 is truly of seamless one-piece construction. In this disclosure and in the claims, "seamless" means that there are no seams of substantial length in the drape, especially no seams running the full side-to-side width of the drape. This is in marked distinction from known drapes, such as the purported "one piece" embodiment of the device described in U.S. Pat. No. 6,019,102, characterized by a side-to-side seam. The inventive drape 20 covers all the critical surfaces of a two-tier cart 10 and yet is of unitary, integral manufacture; the seamless construction not only makes the inventive drape much more less expensive to manufacture, it also eliminates seams that may rip or leak. Further, the unitary configuration of the drape 20 is more easily manipulated into position upon a cart than drapes of known design.

With continued reference to FIG. 1, it is noted that the drape 20 has four principal portions: an upper absorbent portion 22 (corresponding in use generally to the upper surface of the auxiliary shelf 12), a medial portion 24 (which when in use hangs roughly vertically from beneath the auxiliary shelf 12 down to the upper working surface of the main shelf 14), a lower absorbent portion 26 (corresponding in use generally to the upper surface of the main shelf 14), and a lower skirt 28 (which when in use hangs down from the front edge of the main shelf 14). The upper absorbent portion 22 is somewhat larger in areal extent than the upper surface of the auxiliary shelf 12, while the lower absorbent portion 26 very generally corresponds in areal extent to the top surface of the main shelf 14. FIG. 1 illustrates that the upper absorbent portion 22 is folded back against itself and against a segment of the medial portion 24, and the juxtaposed edges are aligned and joined (e.g., by permanent adhesive or by a heat seal) to create parallel side seams or junctures 23, 23', thereby defining an upper pocket or envelope 25 corresponding in size and shape generally to the auxiliary shelf 22. The upper envelope 25 is somewhat larger than the auxiliary shelf 22 so that the envelope 25 can be slipped over and around the auxiliary shelf, as suggested by the dashed lines in FIG. 1. As similarly implied by dashed lines in FIG. 1, the lower absorbent portion 26 can be drawn over and laid upon the main shelf 14.

An inventive method is use to manufacture the drape 20. The method is described with reference made to FIGS. 2–4. The drape 20 everywhere includes a foundation substrate 30 of flexible, liquid-impervious, durable plastic, such as polyethylene or the like. The foundation substrate 30 very preferably is transparent, and may be polyethylene of about 5 mil to 20 mil thickness.

Figure 3:
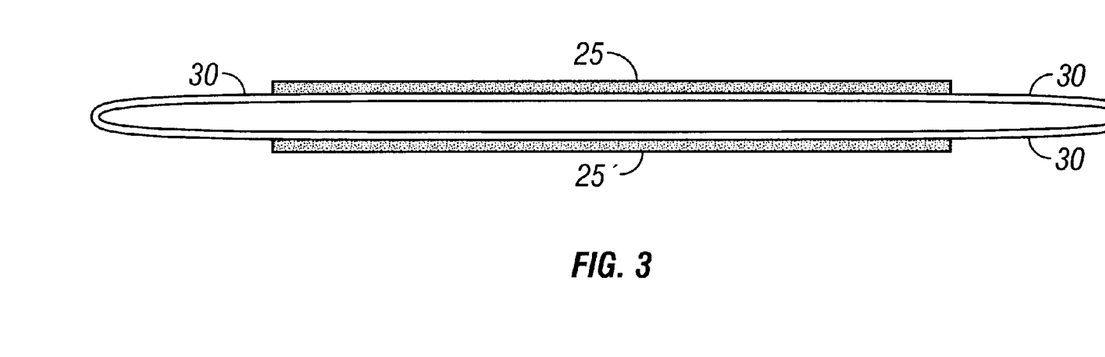
FIG. 3 is an end sectional view of the tubular extension of drape material, similar to the depiction of FIG. 2.
Figure 4:
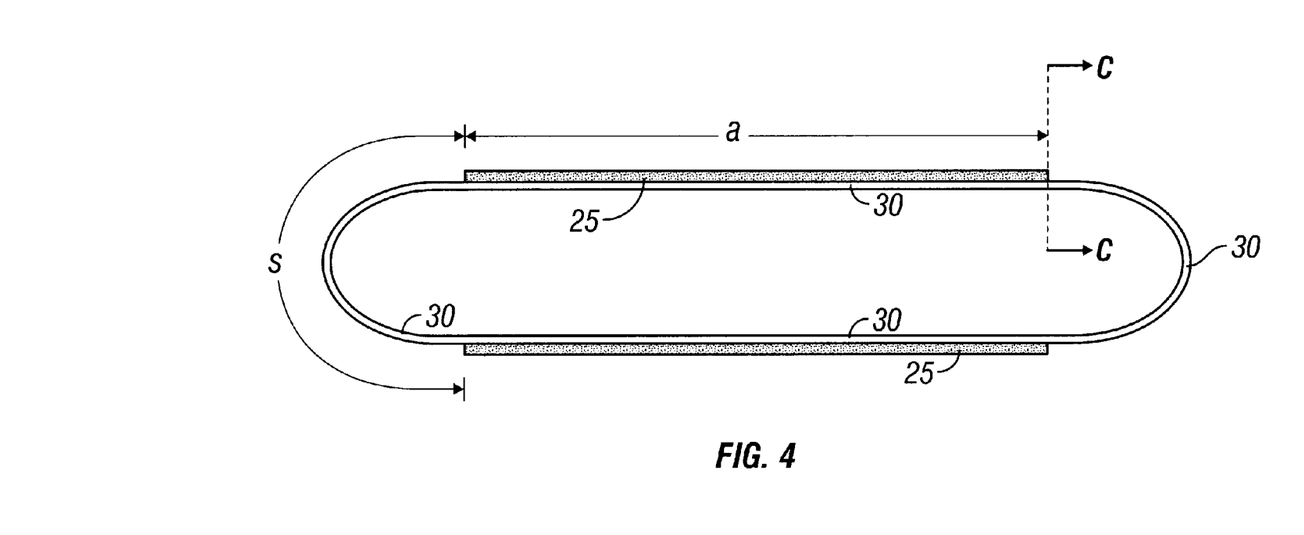
FIG. 4 is another end sectional view of the tubular extension of drape material as seen in FIG. 3, but with the tube expanded to be less oblate.

In a preferred mode of manufacturing the inventive drape 20, the foundation substrate 30 is produced, in a manner known to the art of plastic sheet manufacturing, in a tubular configuration of severely oblate cross section, as seen in FIG. 3. The substrate 30 proceeds from the point of initial production as a tube of indefinite extensive length, and in applications unrelated to the present invention commonly is then completely flattened and rolled onto large spools out from which it may later be paid and used.

Figure 2:
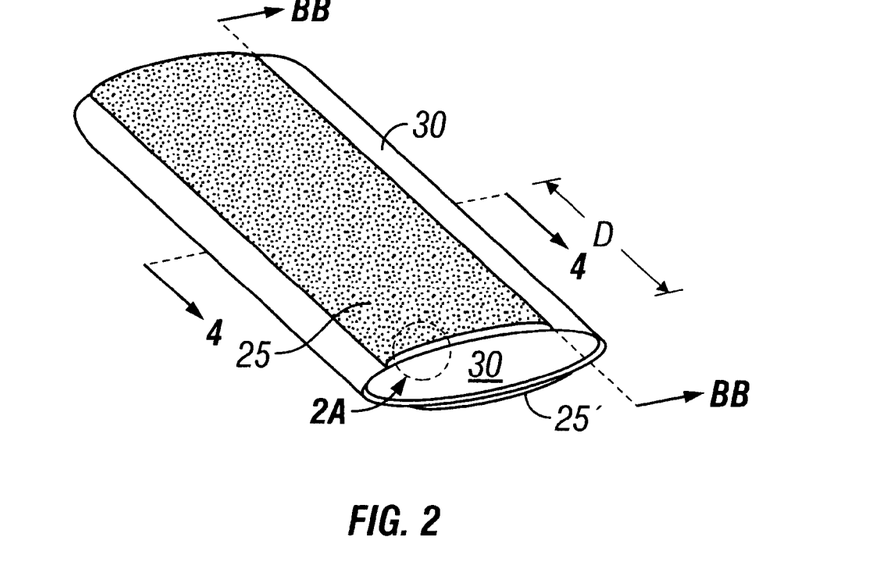
FIG. 2 is a perspective view of a recently manufactured tubular extension of drape material, prior to being cut, suggesting a mode of manufacturing the drape material useable to make the drape apparatus according to the invention.

In the method of the present invention, however, the flexible length of tubular substrate 30 issues from the point of manufacture and is then further processed. After its initial production, the tubular substrate is provided on opposite sides thereof with a pair of two-ply absorbent surfaces 25, 25'. The absorbent surfaces 25, 25' preferably are identical in areal extent and make-up, such that description of one serves to describe both. Referring to FIGS. 2 and 3, the absorbent surfaces 25, 25' are permanently laminated to diametrically opposing sides of the substrate tube. Lamination is accomplished by methods known in the art.

Figure 2A:
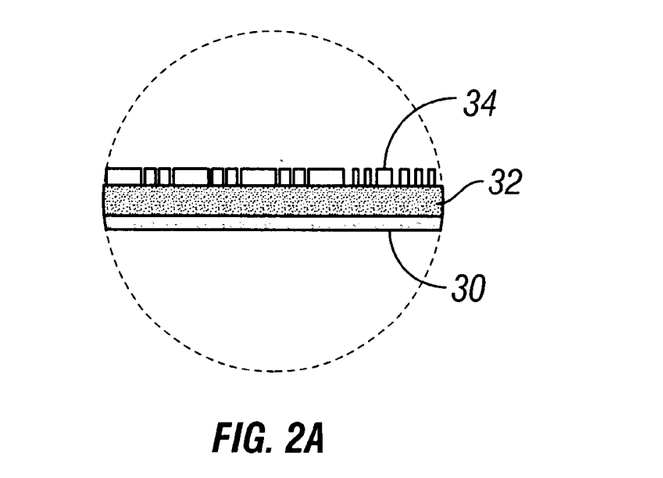
FIG. 2A is an enlarged axial sectional view of an absorbent portion of the drape material depicted in FIG. 2, showing the three-ply character of the absorbent portions of the drape.

Attention is invited to FIG. 2A, an enlarged sectional view of a portion of the substrate 30 to which an absorbent surface 25 has been applied. In a preferred embodiment, the absorbent surface 25 is two-ply, there being an air-laid absorbent layer 32 intermediate between the substrate 30 and a permeable plastic matrix layer 34. The intermediate absorbent layer 32 preferably is a non-woven, liquid-absorbing fabric or paper, preferably of short synthetic fibers, or a mix of natural and synthetic fibers. In the manufacture of the drape material, the absorbent surface 25 preferably is manufactured separately and then adhered to the substrate, but in an alternative method of manufacture the absorbent layer 32 is adhered to the substrate 30, for example by heat pressing, and the matrix layer 34 is then applied. The flexible matrix layer 32 is a permeable plastic (e.g. polyethylene) screen that serves to protect the absorbent layer 32, while yet permitting fluids to pass there through for absorption by the absorbent layer. The matrix layer 34 is a plastic lattice, fully penetrated by preferably uniformly sized (e.g. approximately 0.7 mm to 1.1 mm diameter) and densely and uniformly spaced holes, but the plastic lattice itself offers structural strength and tear-resistance to the layer 34. When adhered by any suitable conventional means, e.g. by heat pressing, to the absorbent layer 32, the matrix layer 34 holds the absorbent layer in place, protects it from scrapes and scuffs, and helps prevent "pull tool" delamination of the absorbent layer or detachment of the absorbent layer 32 from the substrate 30. A very suitable material for the absorbent surface 25 (including an absorbent layer prebonded to a permeable matrix layer) is the SORB-LOC® brand of open-weave absorbent sheet product, manufactured by GOLLAMCO, Inc. of Cincinnati, Ohio.

The dimensions of the various portions of the drape are essentially determined at the time the absorbent surfaces 25, 25' are applied to the substrate 30. The drape may be manufactured in practically any size, and thus may be custom sized to fit any particular cart 10 of any given standard size. A typical cart 10 has a length L (FIG. 1) of about 60 inches. The main shelf 14 commonly is approximately 33 inches, more or less, from front to back (W in FIG. 1), while the auxiliary shelf might be, for example, about 15 inches from front to back (w in FIG. 1).

By way of illustrative but non-limiting example, a drape manufactured to fit the foregoing described cart is cut from a tube having an overall circumference of approximately 114 inches. In such an instance, referring to FIG. 4, the absorbent surfaces are affixed with a width a of approximately 33 inches. The portions of the substrate 30 not covered by absorbent surfaces 25, 25' thus are equal in extent, each having a width s of about 24 inches.

When manufacture of the drape material has been completed with the adhesion of the absorbent surfaces 25, 25' to the substrate 30, a length of the material appears as seen in FIG. 2. Multiple drapes may then be produced by the simple expedient of circumferentially cutting the tubular substrate at suitable intervals, perpendicular to the tube's axis, such as at line AA—AA in FIG. 2. The cutting interval distance D in FIG. 2 corresponds to the length L (side-to-side) of the shelves 12, 14 in FIG. 1, plus an additional length of about 18 inches for a total interval distance D of, for example, approximately 78 inches. The additional length of 18 inches permits the provision of side flaps to be wrapped around the vertical support members 15, 15', as shall shortly be further described. Accordingly, numerous drapes can be quickly and inexpensively mass-produced by being serially cut from a long extension of processed substrate.

Figure 5:
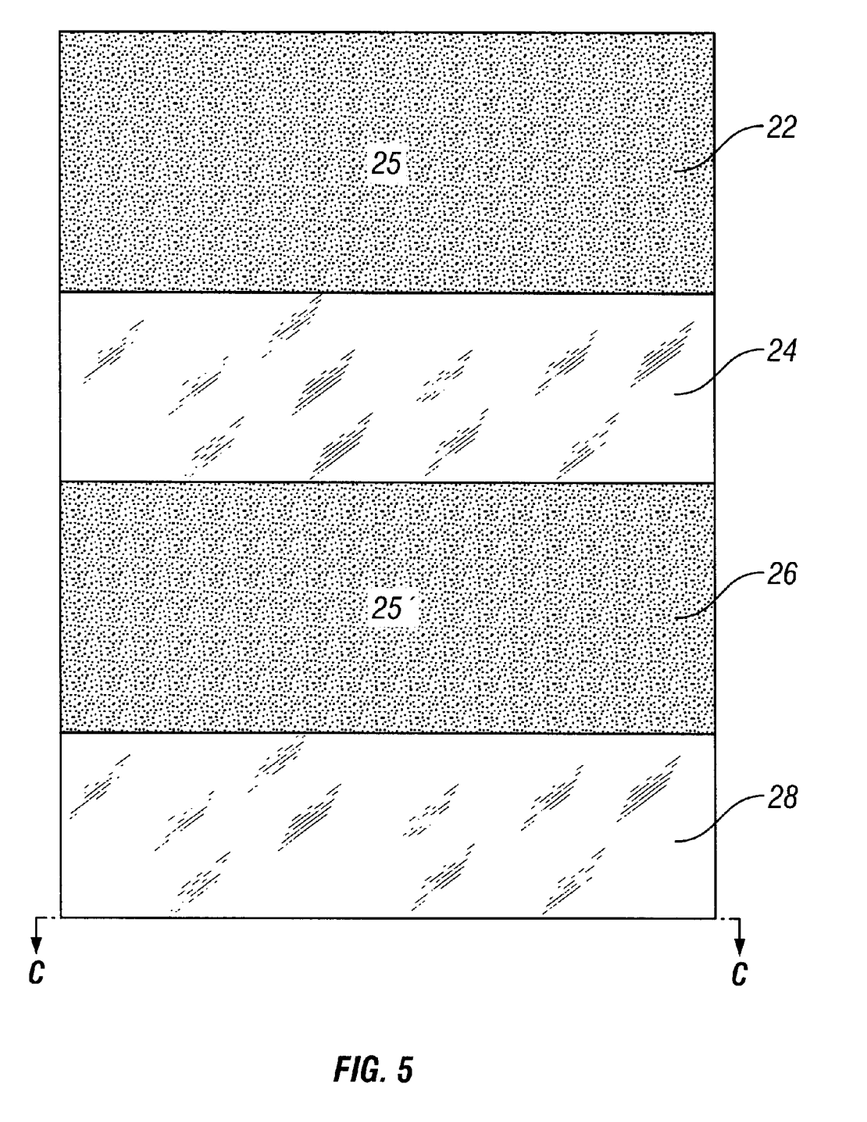
FIG. 5 is a plan view of the drape material of the invention after having been cut laterally and axially from a tube extension of material similar to the depictions of FIGS. 2–4, and according to the method of manufacture of the drape apparatus according to the invention.

Further simplifying the inexpensive manufacture of a drape 20 is that the tubular material is then severed axially along the edge of the upper absorbent surface 25, such as along line BB—BB seen in FIG. 2. Such a cut line corresponds to the location designated at C—C on FIG. 4. The axially severed tube may then be "unrolled," after which it appears as depicted in FIG. 5, with the cut line C—C indicated. The upper absorbent portion 22 has the upper absorbent surface 25 thereon. The medial portion 24 is uncovered, preferably completely transparent, substrate only; the lower absorbent portion 26 is covered with the lower absorbent surface 25'; the lower skirt 28, like the medial portion 24 is naked substrate 30.

Figure 6:
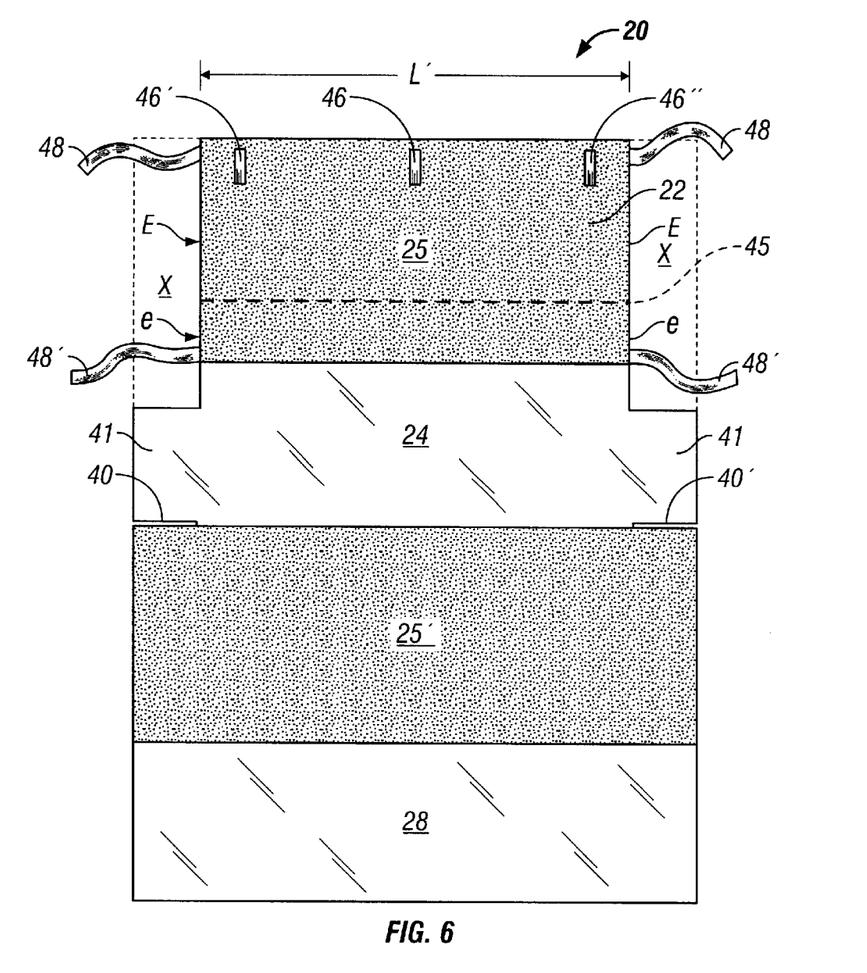
FIG. 6 is a plan view later in time of the drape material as seen in FIG. 5, indicating further cutting and processing steps according to the method of manufacturing the drape of the invention.

The method of manufacture continues with the step of cutting from the drape 20 elongated corner sections X as seen in FIG. 6. Each rectangular offal portion X is cut to have a minor dimension of about 9 inches and a major dimension of approximately 40 inches. Consequently, the upper absorbent portion 22 retains a length L' of about 60 inches, corresponding to the side-to-side width w of the auxiliary shelf 12.

The method also includes the step of making a pair of flap cuts 40, 40' perpendicularly inward from the edge of the drape 20 at the back edge of the lower absorbent portion 26, as indicated in FIG. 6. Flap cuts 40, 40' define flexible flaps 41, 41' that may be wrapped around the vertical support members 15, 15' of the cart when the drape 20 is in use. The upper absorbent portion 22 is then folded at fold line 45, indicated by the heavy dashed line in FIG. 6, to double the upper absorbent portion back against itself, and the edges E are permanently adhered to the edges e to create the permanent junctures 23, 23' seen in FIG. 1. Also, four flexible pull tabs 48, 48' are affixed to the upper absorbent portion 22, for example by securing the proximate ends of the tabs within the junctures 23, 23, as seen in FIG. 1; alternatively, the tabs are simply permanently attached directly to the inner or outer surface of the upper absorbent portion 22. Preferably, the free sections of pull tabs 48, 48' are perforated laterally near the side edges of the upper absorbent portion 22, so that the tabs may be torn and detached after use.

Three double-sided tape strips 46, 46', 46" are then affixed to the upper absorbent portion 22 near its back edge, as seen in FIG. 6. One tape strip 46 is centrally located, and one each 46 and 46" are located near the side edges. The protective shields remain in place on the strips 46, 46', 46" to cover their outer adhesive surfaces until needed, as described hereafter.

With the drape 20 so configured, it appears as seen in FIG. 1, and is ready for installation upon the cart 10.

After manufacture, the drape 20 may be compactly folded and placed in sterile packaging for transportation, storage and sale. The compact folding of the drape 20 preferably leaves the pull tabs 48, 48' exposed so as to be readily identified and grasped when the drape is removed from the sterile packaging.

Upon the preparation of the operating room for surgery, the packaged drape is removed from storage. The new drape 20 may be pulled from its sterile packaging and manipulated by grasping the freely dangling pull tabs 48, 48', which permits the sterile drape to by installed upon a cart 10 by persons with clean but non-sterile hands. Handling only the pull tabs 48, 48', one or preferably two people can unfold and deploy the one-piece drape for installation upon the cart 10. As seen in FIG. 1, the drape 20 is placed upon the cart 10; the upper absorbent portion 22 is pulled over the auxiliary shelf 12 so as smoothly insert the auxiliary shelf into the upper pocket or envelope 25 until the front edge of the auxiliary shelf "bottoms" in the envelope and a portion of the upper absorbent portion may hang over the back edge of the auxiliary shelf (FIG. 7).

Figure 7:
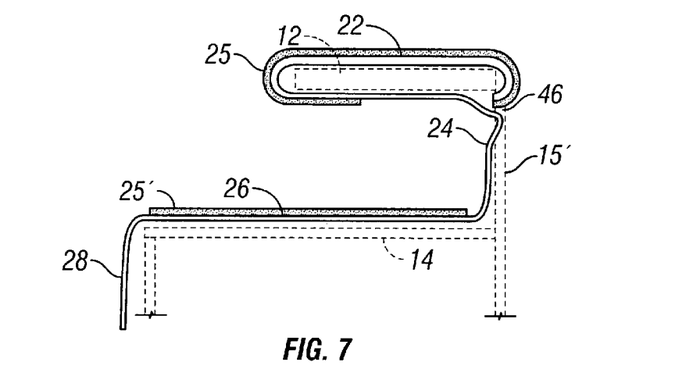
FIG. 7 is a side sectional view (not fully to scale) showing the arrangement of the drape apparatus of the invention upon the shelves of a two-tiered cart of known construction.

Concurrently, the medial portion 24 is drawn back until it hangs vertically adjacent to the supporting members 15, 15' of the cart 10, as seen in the side sectional view of FIG. 7. Also as seen in FIG. 7, the flexible drape 20 consequently is mildly bent or folded to a gently rounded 90-degree angle along the line generally defined by the back edge of the lower absorbent portion 26, so that the back edge of the lower absorbent portion 26 is about parallel adjacent to the back edge of the main shelf 14. The lower absorbent portion 26 lays flat upon the horizontal top surface of the main shelf 14, and the lower skirt portion 28 wraps over the front edge of the main shelf 14 and hangs freely down the front of the cart 10, as indicated by combined reference to FIGS. 1 and 7. It is seen, therefore, that when properly situated upon the cart 10, the upper absorbent portion 22 lays flat upon the tup surface of the auxiliary shelf 12, providing thereon a sterile surface upon which sterilized tools may be arranged. The upper absorbent portion 22, featuring as it does the impermeable substrate 30, supplies protection against instrument strike-through to the auxiliary shelf 12. As it also features the upper absorbent surface 25, the upper absorbent portion 22 sanitarily absorbs any fluids that happen to drip or wipe from the instruments placed thereon, yet the construction of the upper absorbent surface 25 protects against delamination or tearing of the absorbent layer therein.

The medial portion 24 provides a sterile barrier between the working surface of the lower absorbing portion 26 and the cart's non-sterile support members, as suggested by FIGS. 1 and 7. Because the medial portion 24 consists only of foundation substrate, it preferably is transparent, permitting the objects upon the main shelf 14 to be visible from any vantage point around the cart 10, including from the rear.

Numerous surgical instruments may also be arrayed upon the lower absorbent portion 26, horizontally conforming to the top surface of the main shelf 14 as suggested in FIG. 7. The upper absorbent portion 22 lays flat upon the tup surface of the auxiliary shelf 12, providing thereon a sterile surface upon which sterilized tools may be arranged. The lower absorbent portion 26, having the impermeable substrate 30, supplies protection against instrument strike-through to the main shelf 14. As it also features the lower absorbent surface 25', the lower absorbent portion 26 sanitarily absorbs any fluids that happen to fall from instruments placed thereon, yet the construction of the lower absorbent surface 25' protects the absorbent layer therein.

Figure 8:
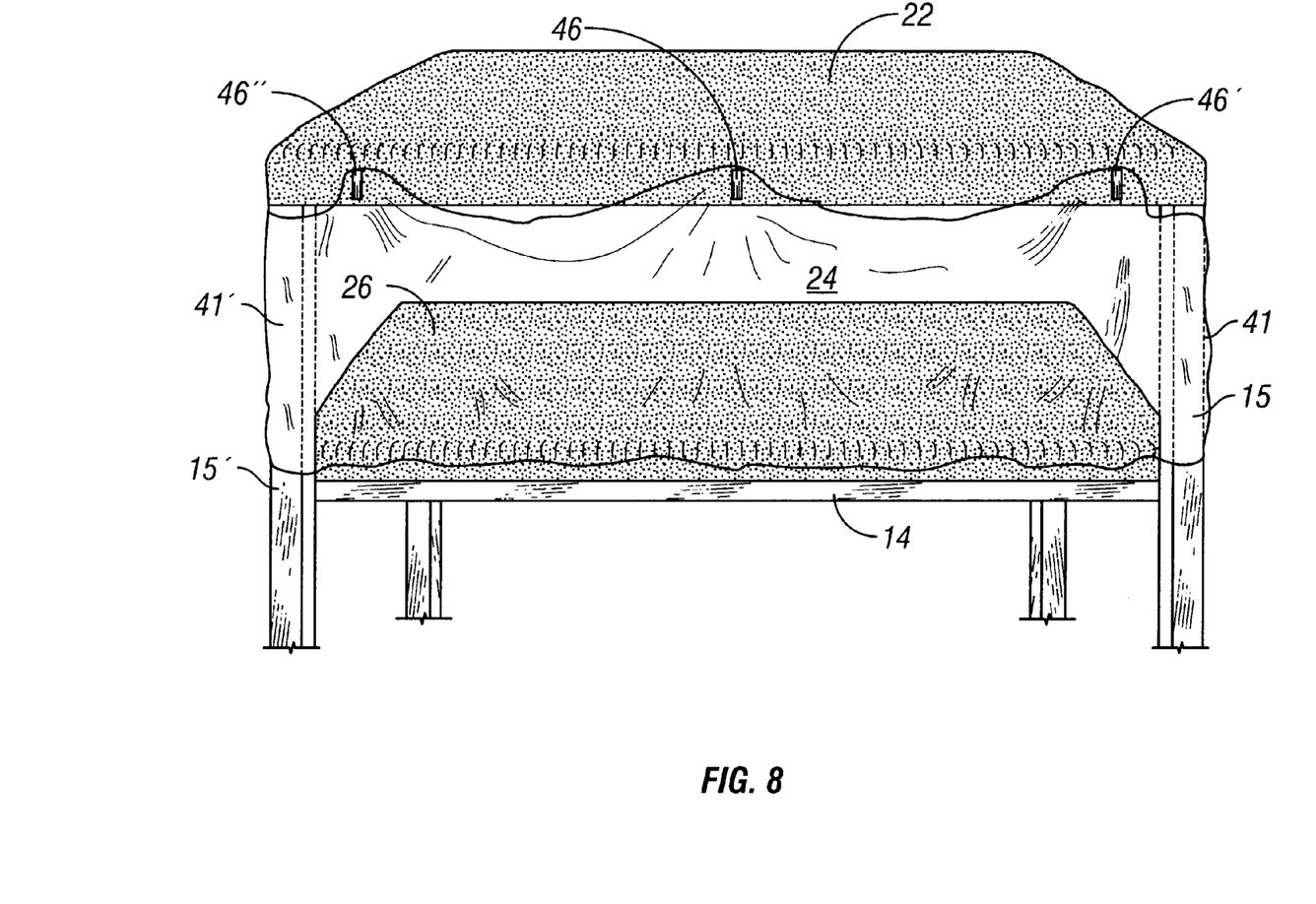
FIG. 8 is a rear view of the inventive drape apparatus according to the invention installed upon a two-tiered cart.

Two final aspects of drape installation upon the cart 10 are best understood with combined reference to FIGS. 1, 6, 7, and particularly FIG. 8. The flaps 41, 41' may be wrapped around the vertical support members 15, 15' to hygienically isolate them. In alternative embodiments, the flaps 41, 41' (or the flaps and the medial portion 24) may be provided with complementary fasteners, such as VELCRO® fabric strips or snaps, to hold the flaps in place around the cart members 15, 15'.

Finally, it is important that the medial portion 24 be held up and back, well away from the lower absorbent portion 26 upon which sterile instruments may be situated. In some known devices, such as the drape of U.S. Pat. No. 6,019,102, this function is realized by the pre-installation of a reusable fastener (e.g. a VELCRO® fabric strip) upon the undersurface of the auxiliary shelf. The pre-installed fastener ostensibly then is engageable with a corresponding complementary fastener upon a portion of the drape to prevent the middle portion of the drape from falling down and forward toward the main shelf of the cart. The pre-installation of fasteners upon the underside of the auxiliary shelf is undesirable from several standpoints. For example, the necessity (but uncertainty) of having the fasteners on the cart and on the drape invariably located in their proper respective locations so as to be mutually engageable. Also, a fastener pre-installed on the cart is used repeatedly, and thus may wear out or become fouled.

The present invention is distinguishable in that it advantageously obviate the need to pre-install any fasteners upon any part of the cart 10. Thus, the inventive drape 20 may be placed upon any style of two-tier cart, without regard for whether or where any pre-installed fasteners are present, or for their condition. Rather, the entire inventive drape 20 is completely disposable, including its fasteners, and when surgery is completed, the entire drape (again including its fasteners) may be removed from the cart 10 and properly disposed of.

Once the drape has been initially situated upon the cart 10, the protective covers are removed from the two-sided adhesive tape strips 46, 46', 46". When the drape is properly installed upon the cart, the tape strips 46, 46', 46" are located at the very back of the auxiliary shelf 12, preferably upon a narrow portion of the upper absorbent portion 22 hanging over the back edge of the auxiliary shelf, as indicated in FIGS. 7 and 8. Continued reference to FIGS. 7 and 8 shows that the medial portion 24 can then be pulled back (e.g. by pinching and grasping its backside, "non-sterile" surface) and brought up, around the back edge of the auxiliary shelf 12, and into adhesive contact with the tape strips 46, 46', 46". The adhesion of the medial portion 24 to the tape strips 46, 46', 46" maintains the medial portion in the proper position (FIG. 7) while the drape is in use upon the cart.

At the conclusion of surgery, the entire drape 20 may be removed from the cart 10 and disposed of according to hospital regulation.

Briefly summarized, an inventive method of manufacturing the drape features the steps of permanently applying absorbent surfaces to opposite sides of a tubular extension of flexible impermeable substrate material; cutting the tube into lengths of material corresponding to the side-to-side width of a cart; cutting the severed piece of material axially along an edge of an absorbent surface, so that the material may be rolled out flat; cutting comers from the rectangular piece of drape material; and cutting flap slots, in order to create side flaps that are wrappable around the vertical support members of the cart; folding an upper absorbent portion back upon itself and joining its edges thereby to define an envelope for receiving a cart's auxiliary shelf; providing the upper absorbent potion with adhesive fasteners, such as two-sided tape strips, to which a medial non-absorbent portion of the drape material may be adhered; and supplying flexible pull tabs extending from the upper absorbent portion and with which the drape may be manipulated.

Accordingly, there is disclosed an inventive drape 20 specially adapted for use with two-tier medical carts or tables. The drape 20 is specially constructed to guard against instrument "strike-through," which may compromise the sterile field of the operating room. The drape according to the invention may be used without breaching standard operating room sterility protocols.

The preferred embodiment of the inventive drape is fitted to cover the auxiliary shelf 12 of popular models of hospital carts. The drape 20 is fashioned from a clear plastic substrate sheet. The clear plastic sheet of the drape 20 is doubled over against itself and its edges sealed along linear junctures 23, 23' to define a pocket or slip-cover portion 25 which slides over the auxiliary shelf 12 from the front thereof. A rear edge of an upper absorbent portion 22 of the drape 20 is provided with double-sided adhesive strips 46, 46", 46" so that the drape 20 may be removably affixed to the cart. Also as shown, a substantial length of the medial portion 24 of the drape extends from the pocket portion 25, down adjacent the shelf legs 15, 15' to the main shelf 14 to assist in maintaining the sterile field.

An advantage of the invention is that the uppermost horizontal planar portion of the drape 20, the portion flush against and generally coextensive with the horizontal surface of the auxiliary shelf 12, has an absorbent surface 25 above the plastic substrate layer. The absorbent surface 25 is the uppermost layer when the drape 20 is in use, while the underlying substrate layer 30 of clear plastic helps prevent undesirable "strike-through" of the drape (e.g. punctures through which bodily fluids may drain from used instruments sitting on the shelf 12), which compromises the sterile field. The drape 20 thus is convenient to use to cover the auxiliary shelf 12; a similarly composed lower absorbent portion 26 offers the same advantages upon the main shelf 14.

Another advantage of the drape 20 is the provision of side flaps 41, 41' which extend laterally to the sides of the medial portion 24. The side flaps 41, 41' may be provided with hook-and-loop fabric fasteners or other suitable fasteners. The flaps 41, 41' are or may be wrapped back around the auxiliary shelf legs 15, 15', as suggested by in FIG. 8. Also, as seen in FIGS. 1 and 6, the drape 20 preferably is provided with pull tabs 48, 48', which permit the drape to be unfolded and manipulated into place upon the cart 10 without direct handling, Thus promoting sterility of the drape's working surfaces. The may also be a back flap provided as an extension of the upper absorbent portion 22, which can be wrapped around the back of the auxiliary shelf 12 and secured to the medial portion 24 by means of two-way tape or other suitable adhesive.

Thus, the use of a special drape 20 upon the cart 10 provides for a sterile operating field.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A drape for use in covering a two-tier medical cart, the cart having a main shelf, an auxiliary shelf, and vertical support members extending between said shelves, the drape comprising:

a seamless foundation substrate comprising a sheet of flexible, impermeable plastic having an upper absorbent portion, a medial portion, a lower absorbent portion, and a lower skirt portion;

a first absorbent surface disposed upon said substrate to define said upper absorbent portion; and a second absorbent surface disposed upon said substrate separate from said first absorbent surface to define said lower absorbent portion;

wherein said medial portion comprises an unperforated portion of said substrate uncovered by an absorbent surface, between said upper absorbent portion and said lower absorbent portion, and wherein said lower skirt comprises a portion of said substrate uncovered by an absorbent surface, and said lower absorbent portion is between said skirt and said medial portion.

2. A drape according to claim 1 wherein said upper absorbent portion comprises side edges and is folded and adhered along said side edges to define an envelope, wherein said envelope corresponds in size to the auxiliary shelf.

3. A drape according to claim 1 wherein said first absorbent surface and said second absorbent surface each comprises a permeable plastic matrix layer and an absorbent layer intermediate between said substrate and said matrix layer, said matrix and absorbent layers pressed parallel together and adhered to said substrate.

4. A drape according to claim 1 further comprising elongated flexible side flaps extending from said medial layer.

5. A drape according to claim 2 further comprising at least two flexible pull tabs, extending from said upper absorbent portion, for allowing said drape to be manipulated without handling said upper absorbent portion, said medial portion, said lower absorbent portion, and said lower skirt portion.

6. A drape according to claim 5 wherein said at least two pull tabs comprise two pairs of pull tabs, a pair extending from opposite sides of said upper absorbing portion.

7. A drape according to claim 5 wherein said at least two pull tabs each comprises a lateral perforation permitting each said tab to be torn along said perforation for detachment from said upper absorbent portion.

8. A drape according to claim 1 further comprising at least one adhesive fastener disposed upon said first absorbent surface on said upper absorbent portion, wherein when said drape is in use, said medial portion may be drawn into adhesive contact with said at least one adhesive fastener to maintain said medial portion pulled away from said lower absorbent portion.

9. A drape for use in covering a two-tier medical cart, the cart having a main shelf, an auxiliary shelf, and vertical support members extending between said shelves, the drape comprising:

a seamless foundation substrate comprising a sheet of flexible, impermeable plastic having an upper absorbent portion, a medial portion, a lower absorbent portion, and a lower skirt portion;

a first absorbent surface disposed upon said substrate to define said upper absorbent portion; and a second absorbent surface disposed upon said substrate separate from said first absorbent surface to define said lower absorbent portion;

wherein said medial portion comprises a portion of said substrate uncovered by an absorbent surface, between said upper absorbent portion and said lower absorbent portion, and wherein said lower skirt comprises a portion of said substrate uncovered by an absorbent surface, and said lower absorbent portion is between said skirt and said medial portion; and wherein said drape further comprises at least one adhesive fastener disposed upon said first absorbent surface on said upper absorbent portion, wherein when said drape is in use, said medial portion may be drawn into adhesive contact with said at least one adhesive fastener to maintain said medial portion pulled away from said lower absorbent portion.

10. A drape according to claim 9 wherein said upper absorbent portion comprises side edges and is folded and adhered along said side edges to define an envelope, wherein said envelope corresponds in size to the auxiliary shelf.

11. A drape according to claim 10 wherein said first absorbent surface and said second absorbent surface each comprises a permeable plastic matrix layer and an absorbent layer intermediate between said substrate and said matrix layer, said matrix and absorbent layers pressed parallel together and adhered to said substrate.

12. A drape according to claim 11 further comprising elongated flexible side flaps extending from said medial layer.

13. A drape according to claim 12 further comprising at least two flexible pull tabs, extending from said upper absorbent portion, for allowing said drape to be manipulated without handling said upper absorbent portion, said medial portion, said lower absorbent portion, and said lower skirt portion.

14. A drape according to claim 13 wherein said at least two pull tabs comprise two pairs of pull tabs, a pair extending from opposite sides of said upper absorbing portion.

15. A drape according to claim 13 wherein said at least two pull tabs each comprises a lateral perforation permitting each said tab to be torn along said perforation for detachment from said upper absorbent portion.

16. A drape for use in covering a two-tier medical cart, the cart having a main shelf, an auxiliary shelf, and vertical support members extending between said shelves, the drape comprising:

a seamless foundation substrate comprising a sheet of flexible, impermeable plastic having an upper absorbent portion, a medial portion, a lower absorbent portion, and a lower skirt portion;

a first absorbent surface disposed upon said substrate to define said upper absorbent portion; and a second absorbent surface disposed upon said substrate separate from said first absorbent surface to define said lower absorbent portion;

wherein said medial portion comprises a portion of said substrate uncovered by an absorbent surface, between said upper absorbent portion and said lower absorbent portion, and wherein said lower skirt comprises a portion of said substrate uncovered by an absorbent surface, and said lower absorbent portion is between said skirt and said medial portion; and further wherein said first absorbent surface and said second absorbent surface each comprises a permeable plastic matrix layer and an absorbent layer intermediate between said substrate and said matrix layer, said matrix and absorbent layers pressed parallel together and adhered to said substrate.

17. A drape according to claim 16 further comprising flexible side flaps extending from said medial layer.

18. A drape according to claim 16 further comprising at least two flexible pull tabs, extending from said upper absorbent portion, for allowing said drape to be manipulated without handling said upper absorbent portion, said medial portion, said lower absorbent portion, and said lower skirt portion.

19. A drape for use in covering a two-tier medical cart, the cart having a main shelf, an auxiliary shelf, and vertical support members extending between said shelves, the drape comprising:
- a seamless foundation substrate comprising a sheet of flexible, impermeable plastic having an upper absorbent portion, a medial portion, a lower absorbent portion, and a lower skirt portion;
- a first absorbent surface disposed upon said substrate to define said upper absorbent portion;
- a second absorbent surface disposed upon said substrate separate from said first absorbent surface to define said lower absorbent portion; and
- at least one adhesive fastener disposed upon said first absorbent surface on said upper absorbent portion, wherein when said drape is in use, said medial portion may be drawn into adhesive contact with said at least one adhesive fastener to maintain said medial portion pulled away from said lower absorbent portion;

wherein said medial portion comprises a portion of said substrate uncovered by an absorbent surface, between said upper absorbent portion and said lower absorbent portion, and wherein said lower skirt comprises a portion of said substrate uncovered by an absorbent surface, and said lower absorbent portion is between said skirt and said medial portion.

20. A drape according to claim 19 further comprising at least two flexible pull tabs, extending from said upper absorbent portion, for allowing said drape to be manipulated without handling said upper absorbent portion, said medial portion, said lower absorbent portion, and said lower skirt portion.

* * * * *